(12) United States Patent
Shirai et al.

(10) Patent No.: US 12,222,309 B2
(45) Date of Patent: Feb. 11, 2025

(54) ELECTRODE SUBSTRATE, METHOD FOR MANUFACTURING SAME, AND BIOSENSOR USING ELECTRODE SUBSTRATE

(71) Applicant: PHC Holdings Corporation, Tokyo (JP)

(72) Inventors: Akihito Shirai, Ehime (JP); Takeshi Hatakeyama, Ehime (JP); Kazuya Kakutani, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 442 days.

(21) Appl. No.: 17/641,528

(22) PCT Filed: Aug. 28, 2020

(86) PCT No.: PCT/JP2020/032501
§ 371 (c)(1),
(2) Date: Mar. 9, 2022

(87) PCT Pub. No.: WO2021/054081
PCT Pub. Date: Mar. 25, 2021

(65) Prior Publication Data
US 2022/0334076 A1     Oct. 20, 2022

(30) Foreign Application Priority Data
Sep. 18, 2019   (JP) .................................. 2019-169161

(51) Int. Cl.
| | | |
|---|---|---|
| *G01N 27/327* | (2006.01) | |
| *A61B 5/145* | (2006.01) | |
| *A61B 5/1486* | (2006.01) | |

(52) U.S. Cl.
CPC ...... *G01N 27/3272* (2013.01); *A61B 5/14532* (2013.01); *A61B 5/14865* (2013.01)

(58) Field of Classification Search
None
See application file for complete search history.

(56) References Cited

U.S. PATENT DOCUMENTS

| | | | |
|---|---|---|---|
| 6,091,078 A | 7/2000 | Codama | |
| 2010/0256064 A1 | 10/2010 | Woolfson et al. | |

(Continued)

FOREIGN PATENT DOCUMENTS

| | | |
|---|---|---|
| CN | 1941384 | 4/2007 |
| EP | 3 494 875 | 6/2019 |

(Continued)

OTHER PUBLICATIONS

International Search Report issued Oct. 20, 2020 in International (PCT) Application No. PCT/JP2020/032501.

(Continued)

*Primary Examiner* — J. Christopher Ball
(74) *Attorney, Agent, or Firm* — Wenderoth, Lind & Ponack, L.L.P.

(57) ABSTRACT

The present disclosure provides an electrode substrate including an insulating substrate having, on a surface thereof, a region where at least one fine uneven structure is formed and a plurality of smooth regions separated by the fine uneven structure; and a conductive thin film formed on the entire of at least one surface of the insulating substrate where the fine uneven structure is formed. According to the present disclosure, the conductive region and the insulating region can be simultaneously formed on the insulating substrate only by forming the conductive thin film in a single step on the entire surface of the single insulating substrate on which the fine uneven structure is formed.

5 Claims, 16 Drawing Sheets

(56) References Cited

U.S. PATENT DOCUMENTS

| | | | |
|---|---|---|---|
| 2012/0078189 A1 | 3/2012 | Ogawa et al. | |
| 2016/0252989 A1 | 9/2016 | Zhang et al. | |
| 2017/0071540 A1 | 3/2017 | Negi et al. | |
| 2017/0128009 A1 | 5/2017 | Pushpala et al. | |
| 2018/0328877 A1 | 11/2018 | Vaddiraju et al. | |
| 2018/0339321 A1 | 11/2018 | Holmes et al. | |
| 2019/0133638 A1 | 5/2019 | Ii et al. | |
| 2019/0352612 A1* | 11/2019 | Abdolahad | C12N 5/0693 |
| 2021/0072179 A1 | 3/2021 | Endoh et al. | |

FOREIGN PATENT DOCUMENTS

| | | |
|---|---|---|
| JP | 11-307240 | 11/1999 |
| JP | 2016-164691 | 9/2016 |
| WO | 2011/078265 | 6/2011 |
| WO | 2013/058879 | 4/2013 |
| WO | 2016/009228 | 1/2016 |
| WO | 2017/187943 | 11/2017 |
| WO | 2019/146788 | 8/2019 |

OTHER PUBLICATIONS

Nakajima, Akira, "Science and Technology of Hydrophobic Solid Surface", Surface Technology, vol. 60, No. 1, 2009, pp. 2-8 (cited in specification).

Japanese Decision of Rejection issued Jun. 6, 2023 in corresponding Japanese Patent Application No. 2021-546573, with English translation.

Extended European Search Report issued Oct. 13, 2022 in European Patent Application No. 20864381.7.

Partial English translation of "Nakajima, Akira, "Science and Technology of Hydrophobic Solid Surface" Surface Technology, 2009, vol. 60, No. 1, pp. 2-8".

International Preliminary Report on Patentability and Written Opinion of the International Searching Authority issued Mar. 15, 2022 in International (PCT) Application No. PCT/JP2020/032501.

* cited by examiner

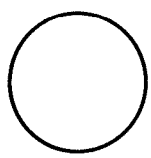 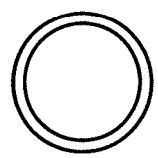 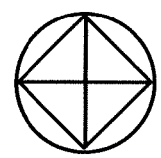
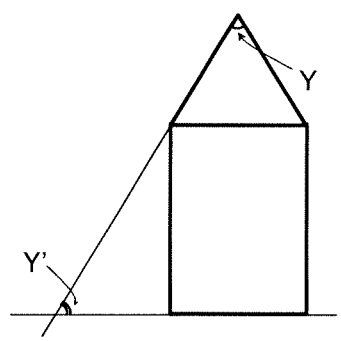 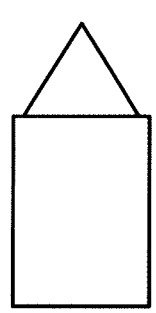 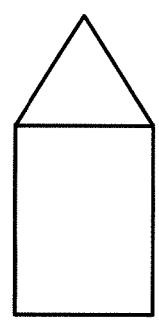
Fig. 5a        Fig. 5b        Fig. 5c

ELECTRODE SUBSTRATE, METHOD FOR MANUFACTURING SAME, AND BIOSENSOR USING ELECTRODE SUBSTRATE

TECHNICAL FIELD

The present disclosure relates to an electrode substrate in which an electric circuit including a conductive thin film, an insulating film, various electrodes, and the like is formed on an insulating substrate, and a method for producing such an electrode substrate. The present invention also relates to a biosensor using such an electrode substrate.

BACKGROUND ART

An electrode substrate is produced by patterning a conductive thin film, an insulating film, or the like formed on an insulating substrate.

For example, in order to form an electrode pattern on the insulating substrate, first, the conductive thin film is formed on the insulating substrate using a technique such as sputtering for conduction. Thereafter, various electrodes are formed at predetermined positions. Finally, for electrode protection, it is common to cover with an insulating material.

When producing an electrode substrate, in order to pattern a conductive thin film and various electrodes into a desired shape, it is common to use various masks including a photoresist film. Such a mask also needs to be removed by peeling or dissolving after patterning.

In recent years, downsizing and weight reduction of various electronic devices have been promoted, and electronic components used therein have also been inevitably reduced, and more precise and highly reliable electrical and electronic circuit designs have been required.

For example, as an electrochemical blood glucose sensor that plays an important role in blood glucose level management in diabetes treatment, an in vivo (implantable) electrochemical glucose sensor that does not cause patient suffering has been developed. The downsizing and weight reduction has been advanced so that the blood glucose level can be measured anytime and anywhere. It is required that an electric/electronic circuit is refined by the downsizing and weight reduction, and measurement accuracy is further improved.

A main body of the in vivo electrochemical glucose sensor is attached to a living body, and a probe on which an electrode containing an analyte-responsive enzyme (for example, GOx and GDH) that specifically reacts with glucose in blood is formed is inserted into the living body to continuously measure a blood glucose level. This makes it possible to measure the blood glucose level over a long period of time without collecting blood each time.

An example of such an in vivo electrochemical glucose sensor is shown in FIG. 1. A probe 11 in which an electric/electronic circuit is formed is attached to a main body 10 of a glucose sensor 1. A tip (sensing part) of the probe 11 is inserted into the living body, and the main body 10 is attached and fixed to the living body 2 (for example, human skin).

The probe 11 is not particularly limited, and is formed using an insulating substrate. The insulating substrate includes a resin substrate as a whole and a stacked substrate in which a resin layer is formed on a glass substrate or a metal substrate as a support. That is, in the present disclosure, the "insulating substrate" means a substrate having an electrical insulation property at least in a surface direction. Although not limited, a working electrode and a reference electrode are formed on one surface of the substrate, and a counter electrode is formed on the other surface. A sensing layer for sensing an electric signal due to a specific reaction between blood glucose and analyte-responsive enzyme is formed on the working electrode. This sensing layer is formed, for example, by appropriately applying an aqueous suspension of conductive particles such as carbon particles, an aqueous solution of analyte-responsive enzyme, and an aqueous solution of redox mediator, and drying them.

In order to produce the probe as described above, first, a conductive thin film is formed on the entire surface of at least one surface of the insulating substrate by depositing a conductive material selected from the group consisting of carbon or a metal such as gold, silver, platinum, or palladium by sputtering, vapor deposition, ion plating, or the like. When a plurality of electrodes are formed on one surface of the substrate, in order to insulate each of the plurality of electrodes, an insulating region is provided on the conductive thin film and divided into a plurality of conductive regions. For example, when the working electrode and the reference electrode are formed on one surface of the substrate, a groove reaching the surface of the insulating substrate is formed in the conductive thin film, and a lead for the working electrode and a lead for the reference electrode are provided. Such a groove is formed by forming a conductive thin film on an insulating substrate and then melting a predetermined region by laser irradiation.

Although fine patterning is required for the demand for downsizing of the electrode substrate, there is a problem that many processes are required for the photoresist and work man-hours are increased. On the other hand, in laser processing, a processing size of about a wiring width and a wiring interval (line/space) on the order of several 10 μm is common. Although a spot diameter on the order of several μm can be set, it is difficult to process into a large area due to the optical system. In addition, a laser device was expensive, and the burden on the producing cost was also large.

CITATION LIST

Patent Literature

Patent Literature 1: WO 2011/078265 A
Patent Literature 2: JP 2016-164691 A

Non Patent Literature

Non Patent Literature 1: Akira NAKASHIMA; Science and Technology of Water-repellent Solid Surface, Surface Technology, Vol. 60, No. 1, 2009, pp. 2-8

SUMMARY OF INVENTION

Technical Problem

The present disclosure provides a technique for easily and stably forming various electrodes in a fine circuit in response to pattern miniaturization due to downsizing of an electrode substrate.

Solution to Problem

Currently, many functional resin films that have a high antireflection function and eliminate glare have been developed. On the surface of such a functional resin film, a fine uneven structure in which bumps of a nano-order size regularly stand is formed. The inventors of the present disclosure have found for the first time that an insulating region can be formed even when a conductive thin film is formed on the surface of a functional resin film having such a fine uneven structure.

The inventors of the present disclosure have further conducted studies, and have succeeded in appropriately designing a smooth region and a fine uneven structure region on an insulating resin substrate and making the smooth region conductive and the region where the fine uneven structure is formed electrically insulating when a conductive thin film is formed thereon.

The fine uneven structure in the present disclosure includes a plurality of protrusions discontinuous in at least one direction in a surface direction (top view) of the insulating substrate. The discontinuous protrusions include a bump and a bank. That is, a structure in which a large number of bumps are discontinuously arranged in at least two directions (FIG. 2a) and a structure in which a large number of jetties are discontinuously arranged in at least one direction (FIG. 2b) are effective as the fine uneven structure of the present disclosure.

In the present disclosure, the "fine" uneven structure is a structure in which a plurality of protrusions are arranged at intervals of submicrons, for example, at intervals of 500 nm or less, and preferably at intervals of 200 nm or less. Note that the arrangement of the bumps or jetties illustrated in FIG. 2 is merely an example. These bumps and jetties can be arranged in combination.

In the present disclosure, the fine uneven structure (C1 or C2 in FIG. 2) in which the plurality of discontinuous protrusions are formed is provided between two smooth regions (A and B in FIG. 2), and when a conductive thin film is formed on the entire surface, the conductive thin film on the region where the fine uneven structure is formed is discontinuous, so that the two smooth regions A and B are electrically insulated from each other.

In the present disclosure, as described above, typically, when a conductive thin film having a thickness of 5 to 100 nm is formed, the fine uneven structure in which the two smooth regions separated by the structure are electrically insulated from each other is referred to as an insulating fine uneven structure.

In the smooth region, structures such as grooves and irregularities having a width and a depth of several nanometers to several hundred microns can be formed as long as the object of the present disclosure is not hindered.

FIG. 3a (cross-sectional view taken along cut line I-I' in FIG. 2a) illustrates a schematic longitudinal sectional view of a bump or a bank constituting the insulating fine uneven structure. The insulating bump or bank has a substantially rectangular longitudinal section.

Hereinafter, the insulating fine uneven structure according to the present disclosure will be further described using a "bump" as an example.

FIGS. 2a and 3a schematically illustrate a fine uneven structure in which a plurality of bumps are arranged. The fine uneven structure formed on the surface of the insulating substrate includes columnar bodies discontinuously arranged in at least one direction. In this specification, the "columnar body" includes a substantially circular column and a substantially prismatic column.

Here, as illustrated in FIG. 4, the "substantially circular column" includes a circular column (a) whose generatrix angle with respect to the axis is 0° and a truncated cone (b) enclosed in a cone having an apex angle X of 10° or less (in the drawing, the angle is exaggerated). When the apex angle X exceeds 10°, the conductive thin film is continuous between adjacent substantially circular columns, and as a result, there is a possibility that the conductive thin film is conducted. A lower bottom surface of the substantially circular column does not have to be an accurate circle, and may be elliptical or amorphous. The "substantially prismatic column" has a shape inscribed in the substantially circular column described above, and the lower bottom surface thereof may also be amorphous instead of a regular polygon.

The circular column or the substantially circular column (columnar body) stands vertically or substantially vertically from the bottom of the fine uneven structure. However, as long as the insulation property of the region where the fine uneven structure is formed and the water repellency to be described later are not affected, even if an upper portion of the circular column or the substantially circular column (columnar body) is refracted or curved, it is allowable.

That is, in the present disclosure, it is important that the conductive thin film formed on the upper bottom surface of one bump and the conductive thin film formed on the upper bottom surface of another adjacent bump are discontinuous when a conductive thin film having a thickness of 5 to 100 nm adopted in producing an ordinary electrode substrate is formed on the surface of the insulating substrate, and for this reason, the substantially circular column (columnar body) includes a circular column (a) whose generatrix angle with respect to the axis is 0° and a truncated cone (b) enclosed in a cone having an apex angle X is 10° or less.

It is sufficient that an intersection angle X' formed by the side of the longitudinal cross-sectional shape of such a circular column or substantially circular column (columnar body) and a horizontal line of the bottom of the fine uneven structure is in the range of 85° to 90°. This will be outlined with reference to FIG. 4(c). FIG. 4c illustrates, by way of example, a substantially circular column that originally stands perpendicular to the bottom but has a refracted or curved top due to a flexible material. At this time, the intersection angle X' between an extension line of the top of the side in the longitudinal cross-sectional shape of the substantially circular column and a line on the surface of the bottom of the fine uneven structure is expressed by (90−X/2°). The apex angle X of the cone is greater than 0° and 10° or less, but the intersection angle X' is 85° or greater and 90° or less in consideration of the circular column. The above geometric relationship can be similarly applied to a case where the axis of the substantially circular column is oblique.

When the columnar bodies are formed so as to satisfy the above requirements, water repellency described later can be imparted to the insulating fine uneven structure region while insulating properties are maintained by molding the tips of the individual columnar bodies into the above shapes.

The insulating fine uneven structure according to the present disclosure is formed of, for example, a columnar body having a diagonal dimension of 10 to 50 nm and a height of 100 to 2000 nm arranged at intervals of 50 to 200 nm as bumps. The substantially circular columns or the substantially prismatic columns may be arranged at regular intervals or may be arranged irregularly. In the structure illustrated in FIG. 2a, the protrusions are aligned vertically and horizontally, but one of the bumps may be arranged alternately either in the vertical or horizontal directions, or may be arranged randomly.

The "interval" between the columnar bodies means a distance between outer edges of the lower bottom surfaces of the columnar bodies. The "diagonal dimension" is the dimension of the lower bottom surface of the columnar body, and means the diameter when the columnar body is substantially circular column and the lower bottom surface is circular, and means a major diameter when the lower bottom surface is elliptical. In addition, in the case of a substantially prismatic column, since the lower bottom surface thereof is polygonal, it means the maximum crossing thereof.

According to the above configuration, the conductive thin film formed on the upper bottom surface of one bump and the conductive thin film formed on the upper bottom surface of another adjacent bump are discontinuous when a conductive thin film having a thickness of 5 to 100 nm adopted in producing an ordinary electrode substrate is formed on the entire surface of the insulating substrate.

This is because that since the upper bottom surface of one bump and the upper bottom surface of the adjacent other bump are separated from each other, when the film thickness of the formed conductive thin film is within the above range, the conductive thin film formed on the upper bottom surface of one bump and the conductive thin film formed on the upper bottom surface of the adjacent other bump are not directly bonded; and since the conductive thin film is not formed on the entire side surface of the bump, the conductive thin film formed on the upper bottom surface of one bump and the conductive thin film formed on the upper bottom surface of another adjacent bump are not indirectly bonded via the conductive thin film formed on the side surface of the bump or the bottom of the fine uneven structure.

Furthermore, as a result of studying the tip shape of each bump constituting the fine uneven structure, it has been found that it is also possible to impart water repellency to the insulating fine uneven structure region while maintaining the insulating properties.

As disclosed in Non-Patent Literature 1, it is known that when a droplet is dropped on a substrate on which a fine uneven structure is formed, depending on the wettability between the material of the substrate and the droplet and the shape of the uneven structure, the wettability is lowered (water repellency is increased) in a case where the fluid exclusion region where the liquid cannot enter the inside of a recess is large, and the Cassie model is applied.

In general, water repellency is determined when $\theta$ is 90° or more, high water repellency is determined when $\theta$ is 110° or more and less than 150°, and super water repellency is determined when $\theta$ is 150° or more.

When there are water droplets on the fine uneven structure, water may not enter the recess and air may exist therein. In such a state, a contact angle $\theta$ of the water droplet on the fine uneven structure is represented by Cassie equation of Equation (1):

[Equation 1]

$$\cos\theta = f\cos\theta_1 + (1-f)\cos\theta_2 \quad (1)$$

Here, $\theta_1$ represents a contact angle with respect to a smooth insulating substrate, $\theta_2$ represents a contact angle with respect to air, and f represents a ratio (0 to 1) of an area of the insulating substrate occupied in the fine uneven structure region. Since the contact angle $\theta_2$ with respect to air is 180°, Equation (1) can be rewritten as Equation (2):

[Equation 2]

$$\cos\theta = f\cos\theta_1 + f - 1 \quad (2)$$

In order to improve the water repellency, it is necessary to reduce f as much as possible and increase the contact angle $\theta$. That is, when the total area of the upper bottom surfaces of the bumps constituting the fine uneven structure is reduced, the water repellency is improved. More specifically, the tip of the bump has a sharp shape.

When an aqueous liquid (aqueous solution or aqueous suspension) is applied to form an electrode, water droplets are not stable on the conductive thin film, and therefore, a mask is required to obtain an electrode having an accurate shape. However, if a region having the water repellency is formed on the insulating substrate to define a region where the electrode is to be formed, it is possible to suppress wet-spreading of the aqueous liquid beyond a water-repellent region without forming a mask.

In the present disclosure, the fine uneven structure having the water repellency as described above is referred to as a water-repellent fine uneven structure.

A cross section of the insulating fine uneven structure having improved water repellency is schematically illustrated in FIG. 3b (a cross-sectional view taken along cut line I-I' in FIG. 2a).

The water-repellent insulating fine uneven structure schematically illustrated in FIG. 3b has a structure in which a cone body having a bottom surface having the same shape as the upper bottom surface or a bottom surface having an area smaller than the upper bottom surface, that is, a substantial cone or a substantial pyramid having a shape inscribed in the substantial cone is coupled to the upper bottom surface of each of the above-described columnar bodies (substantially circular column or substantially prismatic column).

The fine uneven structure formed on the surface of the insulating substrate includes, for example, a bump in which a substantial cone or a substantial pyramid is coupled to an upper bottom surface of a columnar body having a diagonal dimension of 10 to 50 nm and a height of 100 to 2000 nm arranged at an interval of 50 to 200 nm. The substantial cone in FIG. 3b has a bottom surface with a diagonal dimension of 10 to 50 nm. The inward inclination angle of the generatrix of the substantial cone may be larger than the inclination angle of the generatrix of the substantially circular column to which the substantial cone is coupled. For example, an apex angle Y of the substantial cone is 10° to 50°. The axis of the cone body stands perpendicular or substantially perpendicular from the upper bottom surface of the columnar body in which the cone body is formed. However, as long as the insulation property of the region where the fine uneven structure is formed and the water repellency to be described later are not affected, even if an upper portion of the cone body is refracted or curved, it is allowable.

That is, in the present disclosure, when an electrode is formed by applying an aqueous liquid to a surface of an insulating substrate, it is important that the aqueous liquid can be suppressed from wet-spreading beyond a water-repellent region without forming a mask, and for this reason, a cone body includes a cone having an apex angle Y of 10° to 50°.

Considering the case where the upper portion of the circular column or the substantially circular column (columnar body) is refracted or curved, the intersection angle Y' between the side of the longitudinal cross-sectional shape of such a substantial cone (cone body) and the horizontal line of the bottom of the fine uneven structure may be in the range of 65° to 85°.

According to this configuration, the conductive thin film formed on the upper bottom surface of one bump and the conductive thin film formed on the upper bottom surface of another adjacent bump are discontinuous when a conductive thin film having a thickness of 5 to 100 nm adopted in producing an ordinary electrode substrate is formed on the surface of the insulating substrate, and water repellency is obtained. The same applies to the case of a substantial pyramid.

An illustration of the structure of FIG. 3b is illustrated in FIG. 5. FIG. 5a is a schematic longitudinal sectional view of a structure in which a substantial cone having a bottom surface identical in shape to an upper bottom surface of a substantially circular column is coupled to the upper bottom surface of the substantially circular column. FIG. 5b is a schematic longitudinal sectional view of a structure in which a substantial cone having a bottom surface having an area smaller than that of an upper bottom surface of a substantially circular column is coupled to the upper bottom surface of the substantially circular column. FIG. 5c is a schematic longitudinal sectional view of a structure in which a substantial pyramid having a bottom surface having an area smaller than that of an upper bottom surface of a substantially circular column is coupled to the upper bottom surface of the substantially circular column. FIG. 5 illustrates a structure in which the substantial cone or the substantial pyramid is coupled to the upper bottom surface of the substantially circular column, but a structure in which the substantial cone or the substantial pyramid is coupled to the upper bottom surface of the substantially prismatic column is also possible.

In FIG. 3b and FIG. 5, a coupling portion between the substantially circular column and the substantial cone or the substantial pyramid is illustrated as having an angle, but may be smoothly coupled. In addition, the apex of the substantial cone or the substantial pyramid is sharply illustrated, but may have a spherical shape.

Although the bump schematically illustrated in FIG. 2a and FIGS. 3 to 5 has been described, a bank schematically illustrated in FIG. 2b can be used as long as it is common to the bump in the longitudinal cross-sectional shape (cross-sectional view taken along cut line II-II' in FIG. 2b).

That is, the intersection angle X' between the side of the bank in the longitudinal cross-sectional shape and the horizontal plane of the bottom of the fine uneven structure may be 85° to 90°.

The insulating fine uneven structure according to the present disclosure includes, as a bank, a wall body having a bottom width of 10 to 50 nm, a length of 0.1 to 50000 μm, and a height of 100 to 2000 nm arranged at intervals of 50 to 200 nm, for example.

In the fine uneven structure of the present disclosure, the plurality of wall bodies may be linear or curved in the top view, or may be refracted. The wall bodies may be arranged at regular intervals or may be arranged irregularly. In the structure illustrated in FIG. 2b, the wall bodies are arranged side by side, but may be arranged randomly. In addition, in this drawing, the wall body extends continuously from the upper end to the lower end of the region C2, but may be arranged such that wall bodies having a short length are connected.

In the present disclosure, the "longitudinal cross section" of the bump means a cross section including the longitudinal axis of the substantially circular column defined above and taken in parallel with the longitudinal axis. The "longitudinal cross section" of the bank means a cross section when cut perpendicularly to the length direction of the wall body defined above, and when the wall body is curved or bent, the length direction means an extending direction thereof. The "longitudinal cross section" of the cone body is a cross section including the longitudinal axis of the substantial cone defined above and taken in parallel with the longitudinal axis.

In the present disclosure, terms for the shape, for example, the upper bottom surface, the side surface, and the lower bottom surface of the columnar body, the bottom surface and the side surface of the cone body, and the axes thereof are used as meanings usually used mathematically or geometrically.

In the present disclosure, when a numerical range is indicated using the symbol "to", for example, when it is described as "A to B", the numerical values at both ends of the numerical range are included unless otherwise specified. That is, the numerical range "A to B" means "A or more and B or less".

The present disclosure provides a technique capable of simultaneously forming an insulating region and a conductive region and further imparting water repellency to the insulating region when a conductive thin film is formed only by forming a fine uneven structure having a nano-order size in a desired pattern on an insulating substrate, and provides an electrical/electronic circuit with high accuracy simply by using such a technique.

The insulating substrate that can be used in the present disclosure may be flexible or rigid, and is, for example, a resin substrate such as polyethylene terephthalate (PET), polyimide (PI), polyetherimide (PEI), polyamideimide (PAI), a cycloolefin polymer (COP), or polyetheretherketone (PEEK). In addition, a stacked substrate in which a resin film is bonded to a support surface of a glass substrate or a metal substrate can also be used.

In the present disclosure, in order to form a fine uneven structure on a surface of an insulating substrate, a method for pressing a heated mold against a resin substrate or a resin film and thermally transferring the resin substrate or the resin film with a heat press or a heating roll, or a method for pressing a mold against a UV curable resin layer of a stacked film having a UV curable resin layer formed on a base material and irradiating the UV curable resin layer with UV (for example, Patent Literature 1) can be used.

In addition, a processing technique such as laser or a quantum beam or photolithography can be applied to the film surface (Patent Literature 2). Conversely, by irradiating a desired region of the film having the fine uneven structure formed on the entire surface with, for example, $CO_2$ laser or applying a thin film of a resin or metal, the fine uneven structure can be crushed to be macroscopically flat.

Since the smooth region and the fine uneven structure region illustrated in FIG. 2 can be integrally formed on a single insulating substrate in a single step, it is particularly preferable to use a nanoimprinting technique as a method for pressing a mold against the surface of the insulating substrate to form the fine uneven structure.

In the present disclosure, a nanoimprinting technology is used to form a region in which at least one fine uneven structure is formed and a plurality of smooth regions separated by the fine uneven structure on a surface of a single insulating substrate.

Next, a conductive thin film of a conductive material selected from carbon (C) or metals such as gold (Au), silver (Ag), copper (Cu), platinum (Pt), and palladium (Pd) is formed on the entire surface of the insulating substrate. Examples of a method for forming the conductive thin film include a sputtering method, a vapor deposition method, and ion plating.

In the present disclosure, the conductive thin film is formed by depositing the conductive material on the entire surface of the insulating substrate in which a region where the at least one fine uneven structure is formed and a plurality of smooth regions separated by the fine uneven structure are formed, using a sputtering method.

In order to improve the adhesion of the conductive thin film to the insulating substrate, first, the entire surface of the insulating substrate can be subjected to a surface treatment. Examples of the surface treatment method include a plasma treatment such as glow discharge and corona discharge, irradiation with ultraviolet wavelength light using an excimer lamp or the like, and a surface treatment with ozone gas. These surface treatments have an effect of improving the cleanliness of the surface of the insulating substrate and generating a carboxyl group, a hydroxy group, and a carbonyl group, and the surface of the substrate is activated, so that the adhesion of the conductive thin film is improved. Alternatively, the adhesion can be improved by roughening the surface by an etching treatment, a laser irradiation, an ion beam irradiation, a dry or wet blasting treatment, or the like.

In order to improve the adhesion of the conductive thin film to the insulating substrate, although not illustrated, first, a base layer can be formed on the entire surface of the insulating substrate, and the conductive thin film can be formed thereon. As the base layer, a material different from the conductive material for forming the conductive thin film is used in consideration of compatibility between the material of the insulating substrate and the conductive material for forming the conductive thin film. One or more layers of the base layers can be formed. As a material that can be used for the base layer, one or a combination of two or more of chromium (Cr), titanium (Ti), nickel (Ni), aluminum (Al), iridium (Ir), copper (Cu), tungsten (W), indium tin oxide (ITO), silicon dioxide ($SiO_2$), stainless steel SUS, and the like can be used. Among them, chromium (Cr), titanium (Ti), nickel (Ni), and aluminum (Al) are preferable.

Since the conductive thin film can be continuously formed in the same sputtering apparatus while maintaining a vacuum state, it is preferable to use a sputtering method also for forming the base layer.

The thickness of the base layer may be within a range of 10% to 100% of the conductive thin film as long as the object of the present disclosure is not hindered.

The surface treatment and the formation of the base layer may be either one or both, and even if the conductive thin film is directly formed on the surface of the insulating substrate, neither the surface treatment nor the formation of the base layer may be performed as long as there is no problem in adhesion.

In the present disclosure, a method for producing a probe for a biosensor includes a step of forming a conductive thin film of a conductive material selected from carbon or metals such as gold, silver, copper, platinum, and palladium on the entire surface of an insulating substrate having a region where at least one fine uneven structure is formed and a plurality of smooth regions separated by the fine uneven structure on the surface.

According to the producing method of the present disclosure, the conductive region and the insulating region can be simultaneously formed on the insulating substrate only by forming the conductive thin film in a single step on the entire surface of the single insulating substrate on which the fine uneven structure is formed. That is, since the fine uneven structure region is configured to include a plurality of protrusions discontinuous in at least one direction in the surface direction of the insulating substrate, the conductive thin film formed on the region where the fine uneven structure is formed is discontinuous, while the conductive thin film formed on a plurality of smooth regions separated by the fine uneven structure is continuous.

Advantageous Effects of Invention

According to the present disclosure, when a fine uneven structure having a nano-order size in a desired pattern is formed on an insulating substrate and a conductive thin film is formed on the entire surface of the fine uneven structure, a conductive region and an insulating region can be formed at a time without patterning the conductive thin film thereafter, and when water repellency is imparted to the insulating fine uneven structure, an aqueous liquid having high fluidity can be applied to form an electrode pad with high dimensional stability. Therefore, it is possible to form a very fine circuit having a wiring width and a wiring interval (line/space) on the order of several 100 nm with high accuracy even though producing processes and post-processing are reduced, so that it is possible to achieve reduction in process time and improvement in yield in mass production.

BRIEF DESCRIPTION OF DRAWINGS

FIGS. 5a, 5b, and 5c are schematic longitudinal sectional views of an exemplary water-repellent fine uneven structure.

BEST MODE FOR CARRYING OUT THE INVENTION

[Preliminary Experiment 1]

In this preliminary experiment, conductivity and film formation continuity when a conductive thin film was formed on an insulating substrate having a fine uneven structure formed on a surface were checked.

Figure 1:
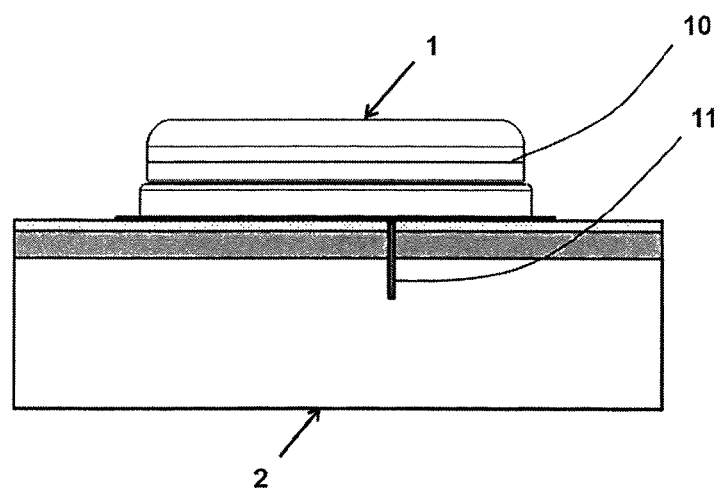
FIG. 1 is a side view illustrating an implantable biosensor in a state of being attached to a living body.
Figures 2A, 2B:
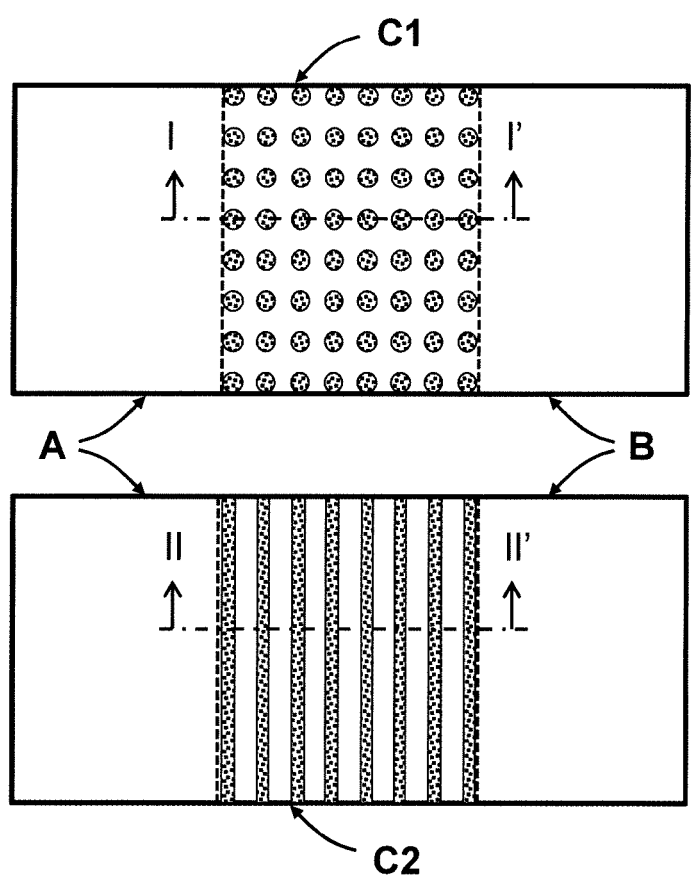
FIGS. 2a and 2b are schematic top views of smooth regions (A and B) and fine uneven structure regions (C1 and C2).
Figure 3A:
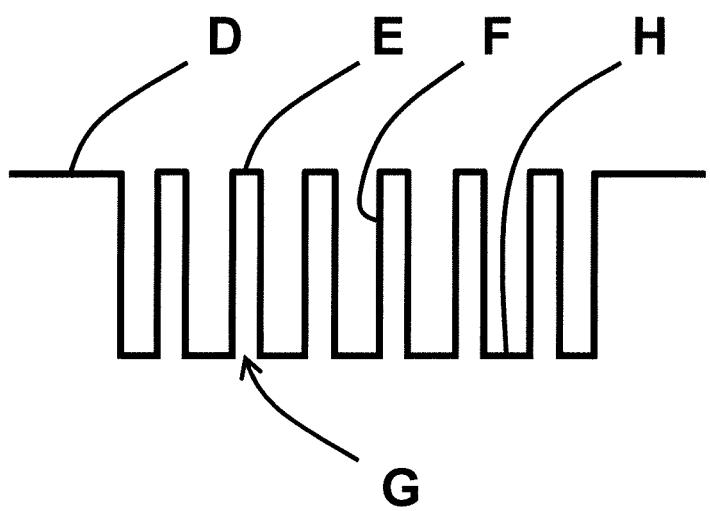
FIGS. 3a and 3b are schematic longitudinal sectional views of the fine uneven structure.
Figure 3B:
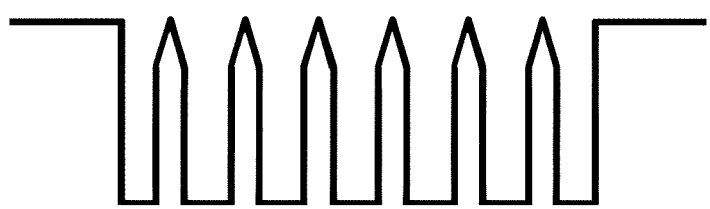
Figures 4A, 4B, 4C:
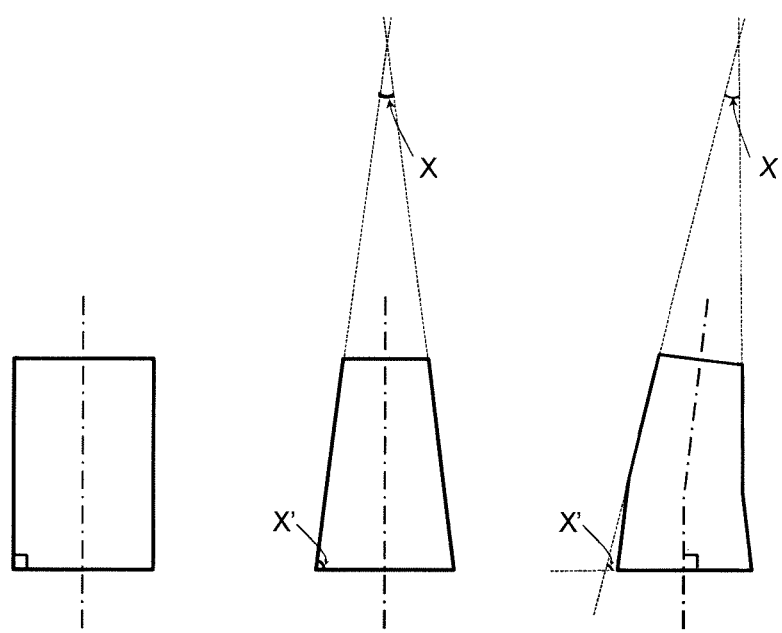
FIGS. 4a, 4b, and 4c are schematic views illustrating a concept of a substantially circular column in the present disclosure.

Au was sputtered to form an Au thin film having a thickness of 5 to 200 nm on the surface of the insulating substrate having the fine uneven structure in which a plurality of bumps schematically illustrated in FIGS. 2a and 3a were arranged. The results of checking the conduction between two smooth regions separated by the fine uneven structure are shown in Table 1. More specifically, the fine uneven structure formed on the surface of the insulating substrate is configured to include substantially circular columns having a diameter of 10 to 50 nm and a height of 100 to 2000 nm arranged at regular intervals of 50 to 200 nm.

TABLE 1

| Au thin film thickness (nm) | Conduction |
| --- | --- |
| 5 | Absence |
| 20 | Absence |
| 50 | Absence |
| 100 | Absence |
| 150 | Presence |
| 200 | Presence |

Figure 6A:
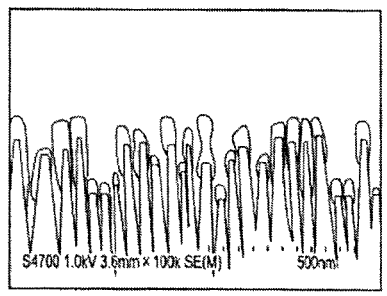
FIGS. 6a and 6b are schematic views illustrating a cross section when Au sputtering is performed on an insulating substrate on which the fine uneven structure is formed: (a) an Au thin film having a thickness of 50 nm and (b) an Au thin film having a thickness of 150 nm are formed on the fine uneven structure region.
Figure 6B:
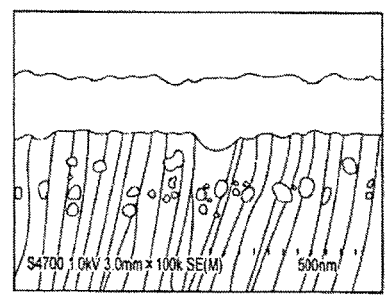

When the thickness of the Au thin film was 100 nm or less, there was no conduction, and when the thickness was 150 to 200 nm, there was conduction. FIG. 6 illustrates a schematic view of an image obtained by observing a cross section of a state in which (a) Au thin films having a thickness of 50 nm and (b) a thickness of 150 nm are formed on the insulating fine uneven structure with an electron microscope (the schematic view was used for improving visibility). It was checked that the Au thin film having a thickness of 50 nm was formed on the tip of each bump forming the fine uneven structure but was discontinuous, and the Au thin film having a thickness of 150 nm was continuously formed over the entire fine uneven structure. This result is consistent with the results of the conductivity test described above.

It has been checked that when an appropriately designed fine uneven structure (for example, the fine uneven structure schematically illustrated in FIG. 3a) is formed on one insulating substrate, even when a conductive thin film having a thickness of 5 to 100 nm usually used in producing an electrode substrate is formed, the conductive thin film formed on the upper bottom surface of each bump constituting the fine uneven structure is not connected, and two smooth regions separated by such a fine uneven structure are electrically insulated.

[Preliminary Experiment 2]

In this preliminary experiment, the visibility when a conductive thin film was formed on an insulating substrate having a fine uneven structure formed on a surface were checked.

Figure 7:
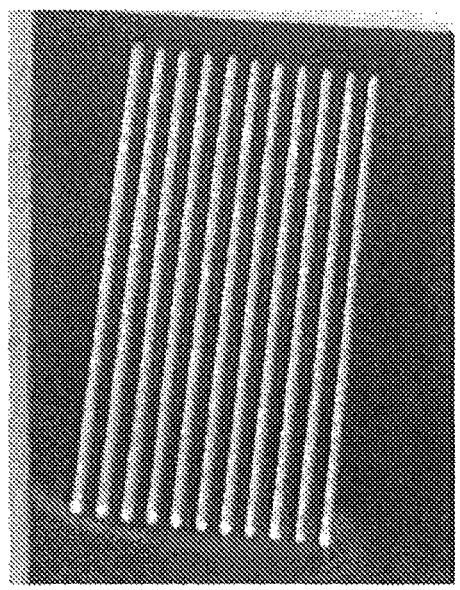
FIG. 7 is a photomicrograph illustrating a surface when an Au thin film is formed on the insulating substrate having the fine uneven structure region formed thereon.

FIG. 7 is a photomicrograph of an upper surface in a state where an Au thin film having a thickness of 50 nm is formed on an insulating substrate having fine uneven structure regions schematically illustrated in FIG. 3a formed, on a surface of the insulating substrate while leaving a plurality of linear regions with a line/space of about 0.2 mm.

It was visually checked that the plurality of linear regions where the fine uneven structure region was not formed were colored with the color of the formed material, and the fine uneven structure region had a lower light reflectance than that of the linear region and was dark in color.

That is, according to the present disclosure, it has been checked that a fine circuit formed by the fine uneven structure can be visually inspected at a stage of forming the conductive thin film.

Based on the findings obtained in the above preliminary experiment, according to a first aspect of the present disclosure, there is provided an electrode substrate including an insulating substrate having, on a surface thereof, a region where at least one fine uneven structure is formed and a plurality of smooth regions separated by the fine uneven structure; and a conductive thin film formed on an entire at least one surface of the insulating substrate where the fine uneven structure is formed, wherein the conductive thin film formed on the region where the fine uneven structure is formed is discontinuous.

In a more specific aspect, the present disclosure provides a probe for a biosensor, including an insulating substrate having, on a surface thereof, a region where at least one fine uneven structure is formed and a plurality of smooth regions separated by the fine uneven structure; a conductive thin film formed on an entire at least one surface of the insulating substrate where the fine uneven structure is formed; and at least one electrode formed in the smooth region separated by the fine uneven structure, wherein the conductive thin film formed on the region where the fine uneven structure is formed is discontinuous, and each of two or more smooth regions separated by the region where the fine uneven structure is formed is electrically insulated.

The fine uneven structure region includes a plurality of protrusions discontinuous in at least one direction in a top view of the insulating substrate. In one aspect, the plurality of protrusions discontinuous in the at least one direction is formed of a columnar body (substantially circular column or a substantially prismatic column) having a diagonal dimension of 10 to 50 nm and a height of 100 to 2000 nm and disposed at intervals of 50 to 200 nm. In another aspect, a substantial cone or a substantial pyramid having a bottom surface having the same shape as the upper bottom surface or a bottom surface having an area smaller than the upper bottom surface is coupled to the upper bottom surface of each of the protrusions.

As a second aspect of the present disclosure, there is provided a method for producing a probe for a biosensor described above. This producing method includes: a step of forming a conductive thin film of a conductive material selected from carbon, gold, silver, copper, platinum, palladium, or the like on the entire surface of an insulating substrate having, on a surface thereof, a region where at least one fine uneven structure is formed and a plurality of smooth regions separated by the fine uneven structure; and a step of forming an electrode in the plurality of smooth regions separated by the fine uneven structure, wherein the fine uneven structure region includes a plurality of protrusions discontinuous in at least one direction in a surface direction (top view) of the insulating substrate, and the conductive thin film formed on the region where the fine uneven structure is formed is discontinuous. As a result, the conductive thin film formed on the upper bottom surface of one protrusion constituting the fine uneven structure region and the conductive thin film formed on the upper bottom surface of another adjacent protrusion are electrically insulated.

As a third aspect of the present disclosure, there is provided a biosensor including the probe for a biosensor described above.

EXAMPLES

An example in which a probe of an in vivo electrochemical glucose sensor is prepared using the above-described technique for forming a fine uneven structure region in a desired pattern will be described below. However, the technology of the present disclosure is not applied only to a glucose sensor, and is useful for producing all electrode substrates in which it is necessary to form a plurality of electrodes on one insulating base material.

1. Method for Producing Probe for Implantable Biosensor

A method for producing a probe 11 of an implantable biosensor 1 according to one embodiment of the present disclosure will be described. The following structure and producing method are one specific example of the present disclosure, and are not limited to the following configuration and producing steps as long as a desired fine uneven structure region having the features of the present disclosure is formed.

Example 1

<Production of Probe>
(1) Preparation of Insulating Substrate

Figure 8A:
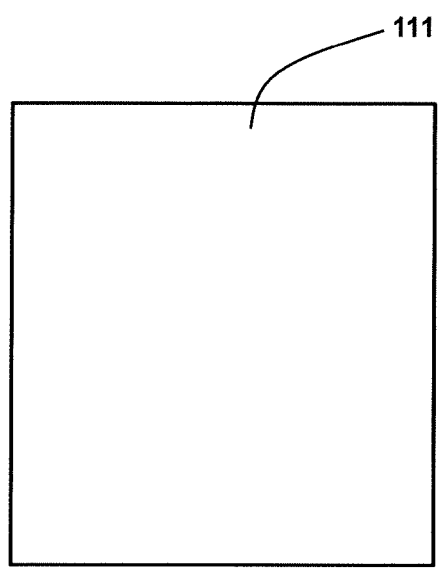
FIGS. 8a and 8b are producing steps of a probe of an implantable biosensor according to a specific example of the present disclosure.

An implantable biosensor 1 includes a main body 10 and a probe 11, and the probe 11 is schematically formed in a key shape including a sensing portion inserted into a living body and a terminal portion electrically connected to an internal circuit of the biosensor main body 10. The sensing portion is formed thin so as to be inserted into the body, and the terminal portion has a constant size so as to be inserted into the biosensor main body 10 to form an electrical connection. First, an insulating substrate 111 is prepared (FIG. 8a, FIG. 11a). The insulating substrate is not particularly limited as long as it is a material and has a thickness that can be used as a probe to be inserted into a living body, and for example, polyethylene terephthalate (PET) having a thickness of about 200 μm can be used. Here, a polyethylene terephthalate (PET) sheet (LUMIRROR R 20 #188 produced by TORAY INDUSTRIES, INC.; 189 μm thick) was used.

(2) Formation of Fine Uneven Structure Region

Figure 8B:
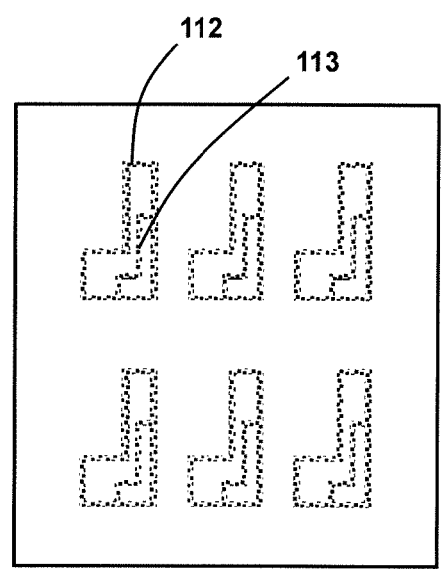
Figure 11:
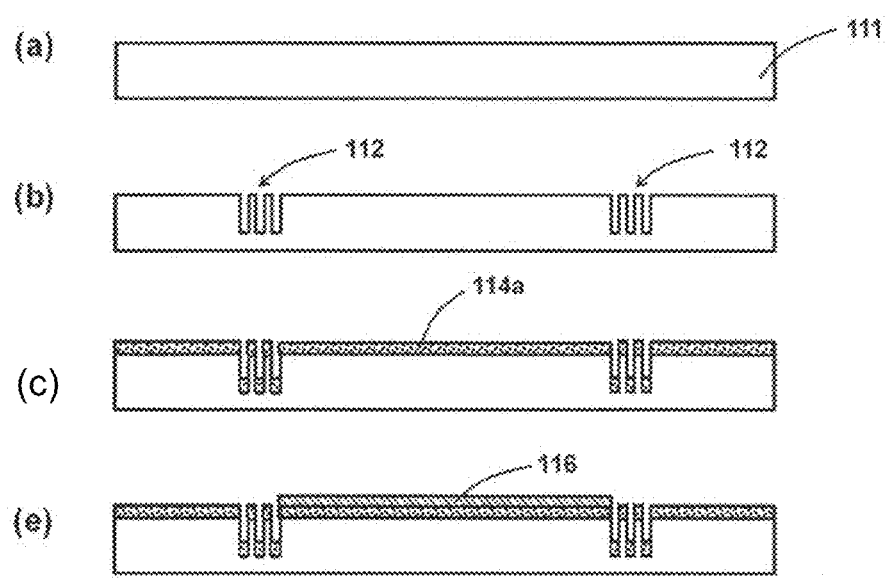
FIGS. 11a-11e cross-sectional views taken along cut line III-III' in FIG. 10e illustrating producing steps (a) to (e).

An insulating fine uneven structure region 112 for forming an outer frame for forming the key-shaped probe 11 is formed on the insulating substrate 111, and an insulating fine uneven structure region 113 for forming an electrode lead for electrically insulating a working electrode lead and a reference electrode lead is formed (FIG. 8b, FIG. 11 b). The insulating fine uneven structure region 113 for forming an electrode lead is essential, but the insulating fine uneven structure region 112 for forming an outer frame may not be formed as desired. The fine uneven structure regions 112 and 113 are of an insulating type.

Such a fine uneven structure region was formed by a nanoimprinting technique in which hot pressing is performed using a mold on which a corresponding fine uneven structure is formed.

(3) Formation of Conductive Thin Film

The conductive thin film 114 is formed on the insulating substrate 111 on which the fine uneven structure region is formed by depositing a conductive material selected from the group consisting of carbon or a metal such as gold, silver, platinum, or palladium by sputtering, vapor deposition, ion plating, or the like. A preferred thickness of the conductive thin film is 5 to 100 nm. In this example, the conductive thin film 114 having a thickness of 100 nm was formed on the insulating substrate 111 by direct gold (Au) sputtering (FIG. 9c, FIG. 11c).

The conductive thin film 114 is divided into a working electrode lead 114a and a reference electrode lead 114b due to the presence of the insulating fine uneven structure region 113 for forming an electrode lead.

(4) Formation of Insulating Film

Figures 9C, 9D:
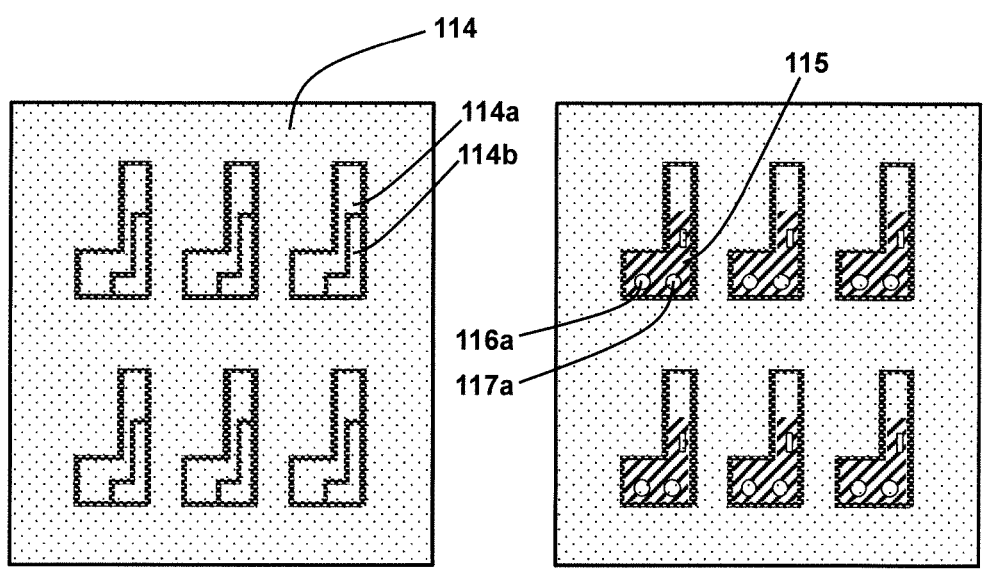
FIGS. 9c and 9d of a probe of an implantable biosensor according to a specific example of the present disclosure.

On the front side of the insulating substrate 111, an insulating film 115a having an opening is formed by a sputtering method, a screen printing method, or the like at a portion excluding regions used as the working electrode 116 and the reference electrode 117, and a working electrode terminal 116a and a reference electrode terminal 117a for electrical connection with the main body 10 (FIG. 9d). A preferred thickness of the insulating film is 0.1 to 40 μm. Here, an insulating film having a thickness of 10 to 20 μm was formed by a screen printing method. As a substitute for the insulating film, an insulating film having the same shape as the insulating film 115a may be attached.

(5) Formation of Sensing Layer

Figure 10E:
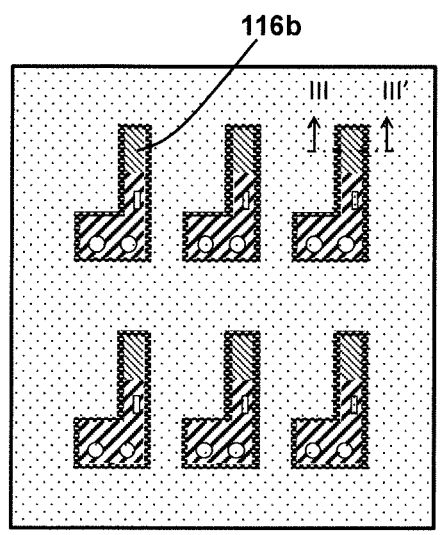
FIGS. 10e and 10f are producing steps of a probe of an implantable biosensor according to a specific example of the present disclosure.

An aqueous solution of a redox mediator and an aqueous solution of an analyte-responsive enzyme are mixed on the conductive thin film 114a of the sensing portion of the probe, which is not covered with the insulating film 115 a, and the mixed aqueous solution is applied and dried to form a sensing layer 116b containing at least the redox mediator and the analyte-responsive enzyme (FIG. 10e, FIG. 11e).

In the present disclosure, the sensing layer may be a multilayer film containing at least a redox mediator and an analyte-responsive enzyme, and formed of a mediator layer containing the redox mediator and an enzyme layer containing the analyte-responsive enzyme by sequentially applying and drying an aqueous solution of the redox mediator and an aqueous solution of the analyte-responsive enzyme. A preferred thickness of the sensing layer is 0.1 to 80 μm.

In addition, in order to improve the conductivity of the sensing layer, conductive particles such as a carbon particle suspension may be applied and dried first before the mixed aqueous solution of the redox mediator and the analyte-responsive enzyme.

In the present disclosure, the "analyte-responsive enzyme" means a biochemical substance capable of specifically catalyzing oxidation or reduction of an analyte. Any biochemical substance may be used as long as it can be used for the sensing purpose of the biosensor. For example, in a case where glucose is used as an analyte, a suitable analyte-responsive enzyme is glucose oxidase (GOx), glucose dehydrogenase (GDH), or the like. The "redox mediator" means an oxidation-reduction substance that mediates electron transfer, and is responsible for transfer of electrons generated by an oxidation-reduction reaction of an analyte in a biosensor. For example, a phenazine derivative and the like are included, but not limited thereto, and any oxidation-reduction substance may be used as long as it can be used for the sensing purpose of a biosensor.

In addition, an example of synthesis of a redox mediator is shown below.

Synthesis Example: Synthesis of Phenazine Derivative Having Carboxyl Group

For example, 5-(4-carboxybutyl)-1-methoxyphenazinium nitrate is synthesized by acting an N-alkylating agent on 1-methoxyphenazine. Furthermore, 5-{[(2,5-dioxopyridin-1-yl) oxy]-5 oxopentyl}-1-methoxyphenazinium nitrate in which N-hydroxysuccinimide is added to the terminal carboxyl group to improve the reactivity of the carboxyl group is synthesized. The corresponding N-alkylating agent can be selected to synthesize a desired N-alkylcarboxyphenazinium salt.

[Chem. 1]

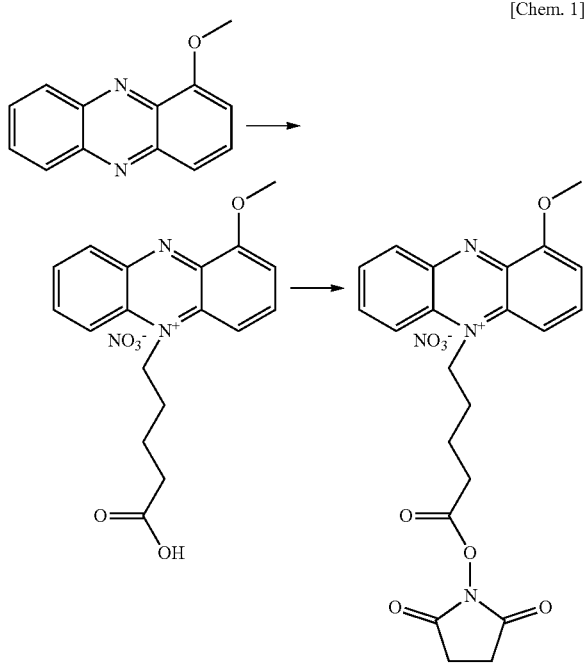

0.6 mg of 5-{[(2,5-dioxopyridin-1-yl) oxy]-5 oxopentyl}-1-methoxyphenazinium nitrate (Ph-C5-Su) obtained in the synthesis example was weighed and dissolved in a 120 µL of 100 mM 2-morpholinoethanesulfonic acid (MES) buffer solution (pH 6.0).

[Chem. 2]

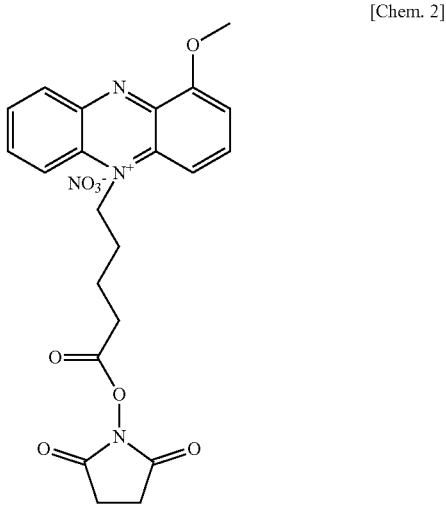

Separately, 5 mg of poly (L-lysine) hydrochloride (Peptide Research Institute Code 3075; M.W.>12000, cut-off by dialysis) was weighed out and dissolved in a 1 mL of 100 mM MES buffer solution (pH 6.0). The two solutions were mixed and reacted at room temperature for 4 hours with stirring.

A reaction solution was subjected to gel filtration chromatography with a PD-10 column (GE Healthcare) using PBS as an elution buffer. The solution after gel filtration was filtrated through a centrifugal ultrafiltration filter (Amicon Ultra-4 30 k; Merck Millipore).

According to the above procedure, a high molecular weight polymer (PLL-05-Ph_1) in which phenazine was covalently bonded to poly (L-lysine) hydrochloride was obtained.

The obtained PLL-05-Ph_1 solution was adjusted to have an absorbance of about 11 at 386 nm with PBS while being measured by a microplate (greiner bio-one UV-STAR MICROPALLETE 96 WELL F-BODEN) and a plate reader (TECAN infinite M 200 PRO). As the absorbance, a value obtained by subtracting the measured absorbance of PBS as a blank value was used.

Here, 0.18 µl of a solution obtained by suspending Ketjen Black EC 600 JD (Lion Specialty Chemicals Co., Ltd.) as a carbon particle suspension at 2 mg/ml with a 0.2% aqueous tetradecyltrimethylammonium bromide (Wako Pure Chemical Industries, Ltd.) solution was applied by an inkjet apparatus (Labojet 3000: produced by Microjet) and dried. Thereafter, 0.12 µl of a mixed aqueous solution of the synthesized PLL-05-Ph_1 as a redox mediator, glucose dehydrogenase (FAD-dependent) (BBI international GDH GLD1) as an analyte-responsive enzyme, and a glutaraldehyde solution (Wako Pure Chemical Industries, Ltd.) was similarly applied by an inkjet apparatus and dried to form a sensing layer 116b having a two-layer structure.

(6) Formation of Reference Electrode

Figure 10F:
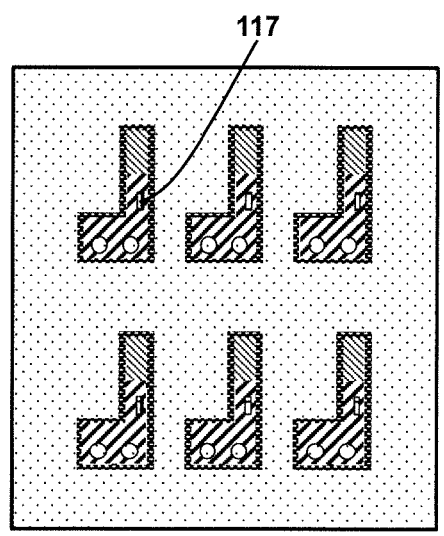

Ag/AgCl is deposited on the reference electrode opening of the insulating film 115a formed on the front side of the insulating substrate 111 by a screen printing method, a dispenser method, or the like to form a reference electrode 117 (FIG. 10f). A preferred thickness of the reference electrode is 5 to 40 µm. Here, Ag/AgCl was deposited by a screen printing method to form a reference electrode (thickness: 10 to 15 µm).

(7) Formation of Counter Electrode

Figure 12G:
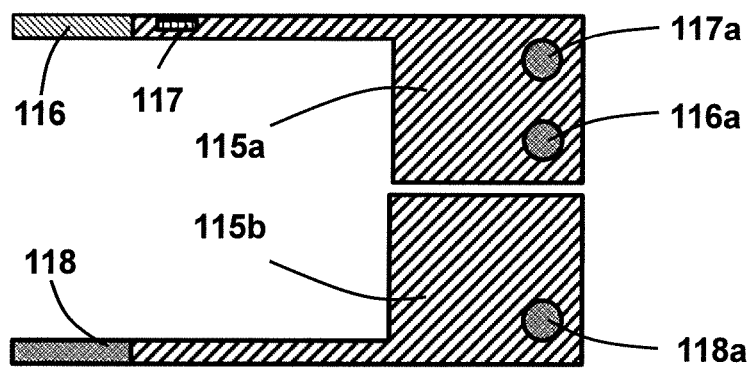
FIGS. 12g and 12h is a producing steps of a probe of an implantable biosensor according to a specific example of the present disclosure.

Although not illustrated in FIGS. 8 to 11, a conductive thin film is also formed on the back side of the insulating substrate 111 in the same step as a case of the front side, an insulating film 115b having an opening is formed by a sputtering method, a screen printing method, or the like in a portion excluding a region used as the counter electrode terminal 118a for electrical connection with the counter electrode 118 and the main body 10, and the conductive thin film 114c of the sensing portion of the probe, which is not covered with the insulating film 115b, is used as the counter electrode 118 (FIG. 12g). In the case of forming a plurality of electrodes on the back side, a desired fine uneven structure is formed in the same step as a case of the front side.

(8) Separation into Individual Probes

Individual probes are separated from the insulating substrate 111 on which the plurality of probes are formed along the insulating fine uneven structure region 112 for forming an outer frame. The probe is separated by cutting the insulating substrate, but a cutting method is not particularly limited, and the probe can be cut by a method known in the art such as laser cutting or die cutting using a pinnacle (registered trademark) die.

One of the isolated probes is shown in FIG. 12. The key-shaped probe 11 is illustrated in a top view as viewed from the front side in an upper part and in a top view as viewed from the back side in a lower part.

(9) Formation of Protective Film

Figure 12H:
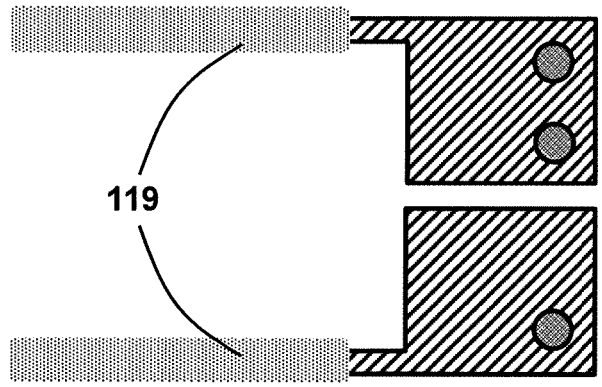

The sensing portion of the probe is immersed in a solution containing a biocompatible resin for sensor protection to form a protective film 119 on both surfaces, side surfaces, and end surfaces of the sensing portion (FIG. 12h). The protective film 119 covers at least the working electrode 116, the reference electrode 117, and the counter electrode 118 without covering the working electrode terminal 116a, the reference electrode terminal 117a, and the counter electrode terminal 118a, and is formed to have a length equal to or longer than the length to be inserted into the living body. A preferred thickness of the protective film is 5 to 200 µm. As the biocompatible resin for sensor protection, although not limited, poly (4-vinylpyridine) can be used, and the poly (4-vinylpyridine) may be crosslinked with a crosslinking agent such as polyethylene glycol diglycidyl ether (PEGDGE), and examples thereof include poly (tert-butyl methacrylate)-b-poly (4-vinylpyridine), polystyrene-co-4-vinylpyridine-co-oligo [propylene glycol methyl ether] methacrylate, and the like.

Here, the sensing portion was immersed in an ethanol solution containing a crosslinking agent and a polymer for a protective film to form a protective film (thickness: 5 to 60 µm) on both surfaces, side surfaces, and end surfaces of the sensing portion. More specifically, a solution obtained by dissolving poly (tert-butyl methacrylate)-b-poly (4-vinylpyridine) (GENERAL SCIENCE CORPORATION) in ethanol so as to be 10% (weight/volume), a solution obtained by dissolving polystyrene-co-4-vinylpyridine-co-oligo [propylene glycol methyl ether] methacrylate) and random (GENERAL SCIENCE CORPORATION) in ethanol so as to be 10% (weight/volume), a solution obtained by dissolving them in poly (ethylene glycol) diglycidyl ether, and a water/ethanol (5/95 volume %) solution of 200 mM 4-(2-hydroxyethyl)-1-piperazineethanesulfonic acid as a buffer solution were prepared, the probe prepared above was immersed in a protective film solution prepared by mixing the solutions, and the probe was repeatedly immersed again 5 to 15 times after drying for 10 minutes and dried for 24 hours or more, so that a crosslinked protective film was formed to obtain a probe.

2. Internal Structure of Probe of Implantable Biosensor

An internal structure of the probe 11 of the implantable biosensor 1 according to one embodiment of the present disclosure will be further described.

Figure 13:
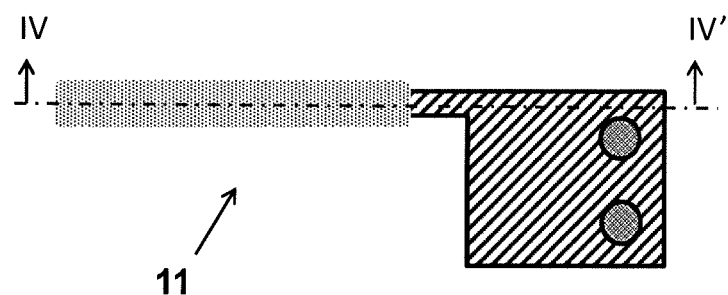
FIG. 13 is a top view of a probe front side of an implantable biosensor according to a specific example of the present disclosure.
Figure 14:
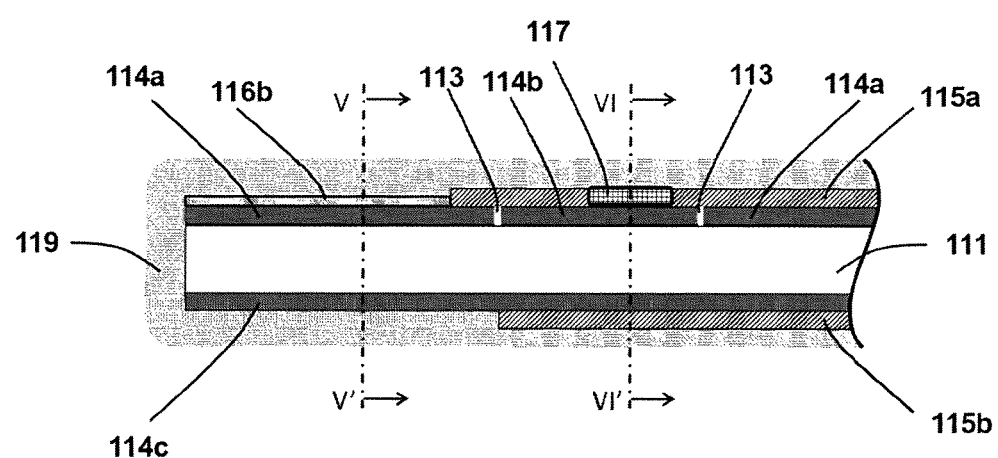
FIG. 14 is a cross-sectional view taken along cut line IV-IV' in FIG. 13.

FIG. 13 is a top view of the probe 11 completed up to formation of the protective film as viewed from the front side. FIG. 14 is a cross-sectional view taken along cut line IV-IV' in FIG. 13. The conductive thin films 114 are formed on both sides of the insulating substrate 111. The conductive thin film 114 on the front side is separated into two electrode leads, that is, the working electrode lead 114a and the reference electrode lead 114b by the insulating fine uneven structure region 113 for forming an electrode lead, and is electrically insulated. The sensing layer 116b is formed on a partial region of the working electrode lead 114a. In addition, the reference electrode 117 is formed in the opening portion of the insulating film 115a, and is electrically connected to the reference electrode lead 114b. The conductive thin film 114 on the back side serves as a counter electrode lead 114c, and a part thereof functions as the counter electrode 118.

Figure 15:
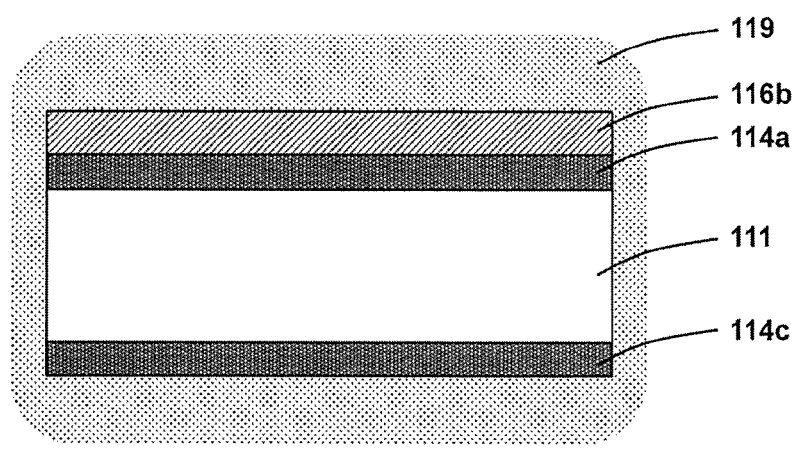
FIG. 15 is a cross-sectional view taken along cut line V-V' in FIG. 14.

FIG. 15 is a cross-sectional view taken along cut line V-V' in FIG. 14. The working electrode lead 114a is formed on the front side of the insulating substrate 111, and the sensing layer 116b is formed thereon. A counter electrode lead 114c is formed on the back side of the insulating substrate 111. Furthermore, it can be seen that the entire periphery of the sensing portion is covered with the protective film 119.

Figure 16:
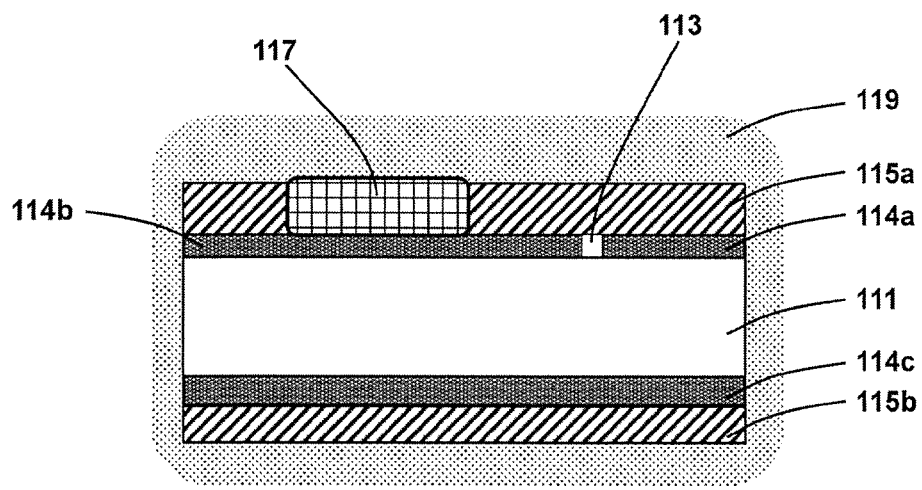
FIG. 16 is a cross-sectional view taken along cut line VI-VI' in FIG. 14.

FIG. 16 is a cross-sectional view taken along cut line VI-VI' in FIG. 14. On the front side of the insulating substrate 111, the working electrode lead 114a and the reference electrode lead 114b electrically separated by the insulating fine uneven structure region 113 for forming an electrode lead are formed, and an insulating film 115a is formed thereon. The reference electrode 117 is formed in the opening of the insulating film 115a. The counter electrode lead 114c is formed on the back side of the substrate 111, and the insulating film 115b is formed thereon. Furthermore, it can be seen that the entire periphery of the sensing portion is covered with the protective film 119 of the present disclosure.

3. Preparation of Biosensor

The completed probe 11 was attached to the biosensor main body 10 to produce an implantable biosensor.

INDUSTRIAL APPLICABILITY

According to the present disclosure, since the insulating substrate on which the fine uneven structure region appropriately designed in a nanosize is formed is used, it is possible to produce an electrode substrate including a very fine circuit having a wiring width and a wiring interval (line/space) on the order of several hundreds of nm. The miniaturization can also contribute to downsizing of the sensor. In addition, it is also possible to arrange a plurality of electrodes in a conventional size, which can also contribute to producing of a multifunctional sensor. Regarding the producing method, since the circuit patterning is performed on the insulating substrate in advance using the nanoimprinting technology, the number of producing steps is reduced, and thereby the producing cost can be reduced. In addition, since the fine uneven structure is patterned by transferring a mold, dimensional variations in producing are small, and mass production with stable circuit dimensions is possible. Further, when the conductive thin film having a thickness of 5 to 100 nm is formed on the fine uneven structure region, the reflectance of light is different between the fine uneven structure region and the smooth region where the fine uneven structure is not formed, so that a fine circuit can be checked using a camera or the like at a stage of forming the conductive thin film. With this feature, a circuit failure can be found before proceeding to a subsequent step, and thus the yield is improved.

REFERENCE SIGNS LIST

1 Implantable biosensor
10 Main body
11 Probe
111 Insulating substrate
112 Insulating fine uneven structure region for forming outer frame
113 Insulating fine uneven structure region for forming electrode lead
114 Conductive thin film
114a Working electrode lead
114b Reference electrode lead
114c Counter electrode lead
115 Insulating film
116 Working electrode
116a Working electrode terminal
116b Sensing layer
117 Reference electrode 117a Reference electrode terminal
118 Counter electrode
118a Counter electrode terminal
119 Protective film
2 Living body
A First smooth region
B Second smooth region
C1 Fine uneven structure region of first embodiment
C2 Fine uneven structure region of second embodiment
D Smooth region of insulating substrate
E Upper bottom surface of protrusion (upper side in longitudinal sectional view)
F Side surface of protrusion (side in longitudinal sectional view)
G Lower bottom surface of protrusion (lower side in longitudinal sectional view)
H Bottom portion of fine uneven structure

The invention claimed is:

1. An electrode substrate comprising:

an insulating substrate having, on a surface thereof, a region where a fine uneven structure is formed and a plurality of smooth regions separated by the fine uneven structure; and a conductive thin film formed on an entirety of at least one surface of the insulating substrate where the fine uneven structure is formed, wherein the conductive thin film formed on the region where the fine uneven structure is formed is discontinuous, wherein the fine uneven structure region includes a plurality of protrusions discontinuous in at least one direction in a surface direction of the insulating substrate, wherein the plurality of protrusions discontinuous in the at least one direction include columnar bodies, and for each columnar body, an intersection angle X' between a side of the columnar body in a longitudinal cross-sectional shape and a line on a surface of a bottom of the fine uneven structure is 85° to 90°, wherein each columnar body has a diagonal dimension of 10 to 50 nm and a height of 100 to 2000 nm, and the columnar bodies are disposed at intervals of 50 to 200 nm, wherein each columnar body includes a substantial cone or a substantial pyramid coupled to an upper surface of the columnar body, the substantial cone or the substantial pyramid having a bottom surface which has the same shape as the upper surface of the columnar body or which has an area smaller than that of the upper surface of the columnar body.

2. The electrode substrate according to claim 1, wherein each columnar body is a substantially circular column or a substantially prismatic column, and an inward inclination angle of a generatrix of the substantial cone or a side surface of the substantial pyramid is larger than an inclination angle of a generatrix of the substantially circular column or a side surface of the substantially prismatic column to which the substantial cone or the substantial pyramid is coupled.

3. The electrode substrate according to claim 1, wherein the plurality of protrusions discontinuous in the at least one direction include wall bodies, and for each wall body, an intersection angle X' between a side of the wall body in a longitudinal cross-sectional shape and a line on a surface of a bottom of the fine uneven structure is 85° to 90°.

4. The electrode substrate according to claim 3, wherein each wall body has a bottom width of 10 to 50 nm, a length of 0.1 to 50000 μm, and a height of 100 to 2000 nm, and the wall bodies are arranged at intervals of 50 to 200 nm.

5. The electrode substrate according to claim 1, wherein a thickness of the conductive thin film formed in a region where the fine uneven structure is formed is 5 to 100 nm.

* * * * *